United States Patent
Ervin et al.

(10) Patent No.: US 8,334,024 B1
(45) Date of Patent: *Dec. 18, 2012

(54) METHOD AND APPARATUS FOR SINGLE SIDE BILAYER FORMATION

(75) Inventors: Eric N Ervin, Park City, UT (US); Geoffrey Alden Barrall, San Diego, CA (US)

(73) Assignee: Electronic Bio Sciences, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/362,806

(22) Filed: Jan. 31, 2012

Related U.S. Application Data

(63) Continuation of application No. 12/325,792, filed on Dec. 1, 2008, now Pat. No. 8,124,191.

(60) Provisional application No. 60/991,542, filed on Nov. 30, 2007.

(51) Int. Cl.
*B05D 1/18* (2006.01)
(52) U.S. Cl. ............ 427/430.1; 427/299; 427/435; 427/443.2
(58) Field of Classification Search ............ 427/430.1, 427/434.2
See application file for complete search history.

(56) References Cited

U.S. PATENT DOCUMENTS

| | | | |
|---|---|---|---|
| 4,824,529 A | 4/1989 | Thompson et al. | |
| 5,378,342 A | 1/1995 | Ikematsu et al. | |
| 6,074,611 A | 6/2000 | Flesher | |
| 7,777,505 B2 * | 8/2010 | White et al. | 324/693 |
| 2004/0055901 A1 | 3/2004 | Petersen et al. | |
| 2005/0191616 A1 | 9/2005 | Shenoy et al. | |
| 2008/0153150 A1 | 6/2008 | Holden et al. | |

FOREIGN PATENT DOCUMENTS

| | | |
|---|---|---|
| EP | 1710578 | 10/2006 |
| WO | WO 2006/100484 | 9/2006 |
| WO | WO 2006/104639 | 10/2006 |

OTHER PUBLICATIONS

Bayley et al., "Stochastic Sensors Inspired by Biology", Nature, vol. 413, pp. 226-230, 2001.

(Continued)

*Primary Examiner* — David Turocy
(74) *Attorney, Agent, or Firm* — Diederiks & Whitelaw, PLC

(57) ABSTRACT

An apparatus for single-sided bilayer formation includes a first fluid chamber including a sidewall and a second fluid chamber extending through the sidewall. A barrier wall, having at least a portion defining a hydrophobicity or hydrophilicity surface property, separates the first and second fluid chambers and includes a nanopore therein across which a planar lipid bilayer (PLB) is formed. In use, an electrolyte is added to the first and second fluid chambers and a lipid/organic solvent mixture is added to the first fluid chamber to form a lipid/organic solvent layer. The electrolyte level within the first fluid chamber is adjusted such that the lipid layer is raised above the barrier wall and a PLB is formed through single-sided spontaneous formation from the first fluid chamber across the nanopore.

19 Claims, 6 Drawing Sheets

OTHER PUBLICATIONS

Coronado et al., "Phospholipid Bilayers Made From Monolayers on Patch-Clamp Pipettes", Biophysical Journal, vol. 43, pp. 231-236, 1983.

Miller, "Ion Channel Reconstruction", Plenum Press, pp. 3-35, 1986.

Montal et al, "Formation of Bimolecular Membranes from Lipid Monolayers and a Study of Their Electrical Properties", Proc. Nat. Acad. Sci. USA, vol. 69, No. 12, pp. 3561-3566, 1972.

Mueller et al., "Methods for the Formation of Single Bimolecular Lipid Membranes in Aqueous Solution", J. Phys. Chem., vol. 67, pp. 534-535, 1963.

Schindler, "Formation of Planar Bilayers from Artificial or Native Membrane Vesicles", FEBS Letters, vol. 122, No. 1, pp. 77-79, 1980.

Suzuki et al., *Planar Lipid Bilayer Reconstruction with a Microfluidic System*, Lap. Chip., pp. 502-505, 2004.

White et al., "Single Ion-Channel Recordings Using Glass Nanopore Membranes", J. Am. Chem. Soc., vol. 129, No. 38, pp. 11766-11775, 2007.

* cited by examiner

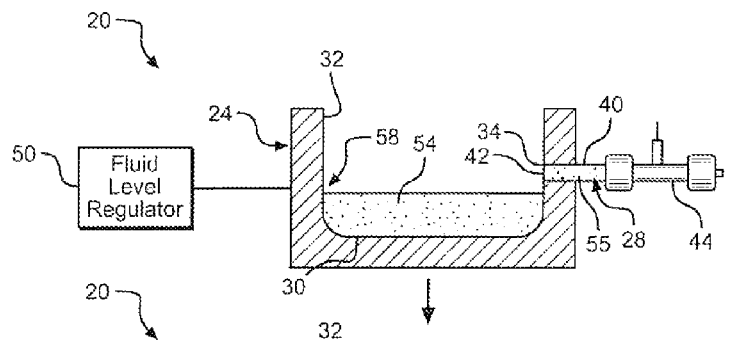
FIG. 1A
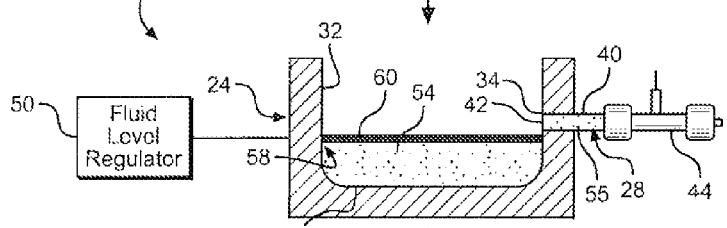
FIG. 1B
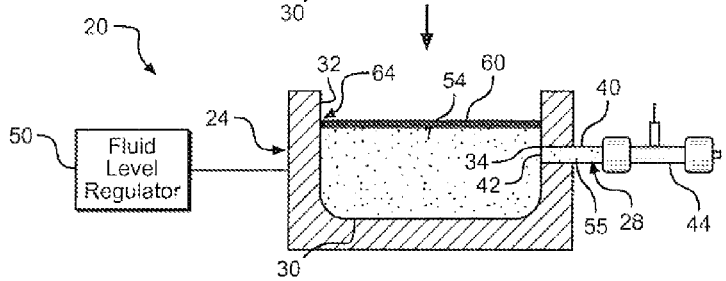
FIG. 1C
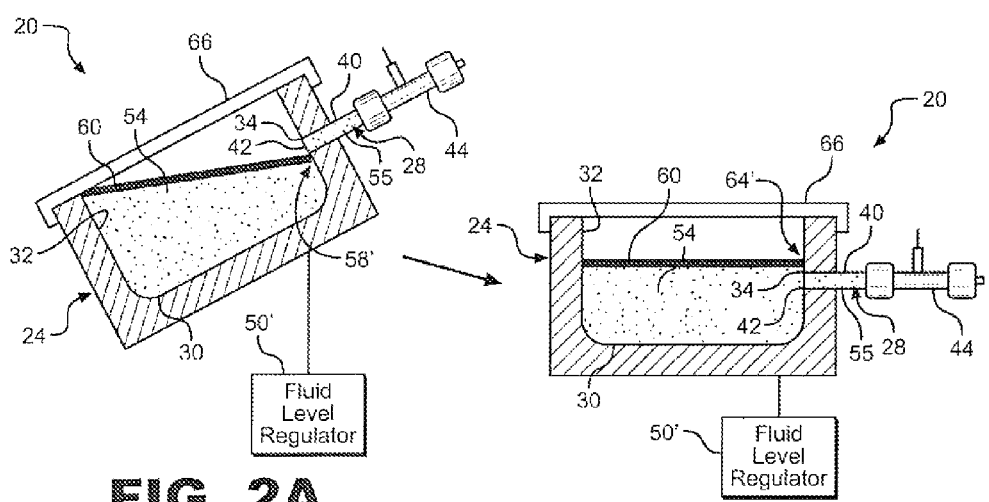
FIG. 2A
FIG. 2B

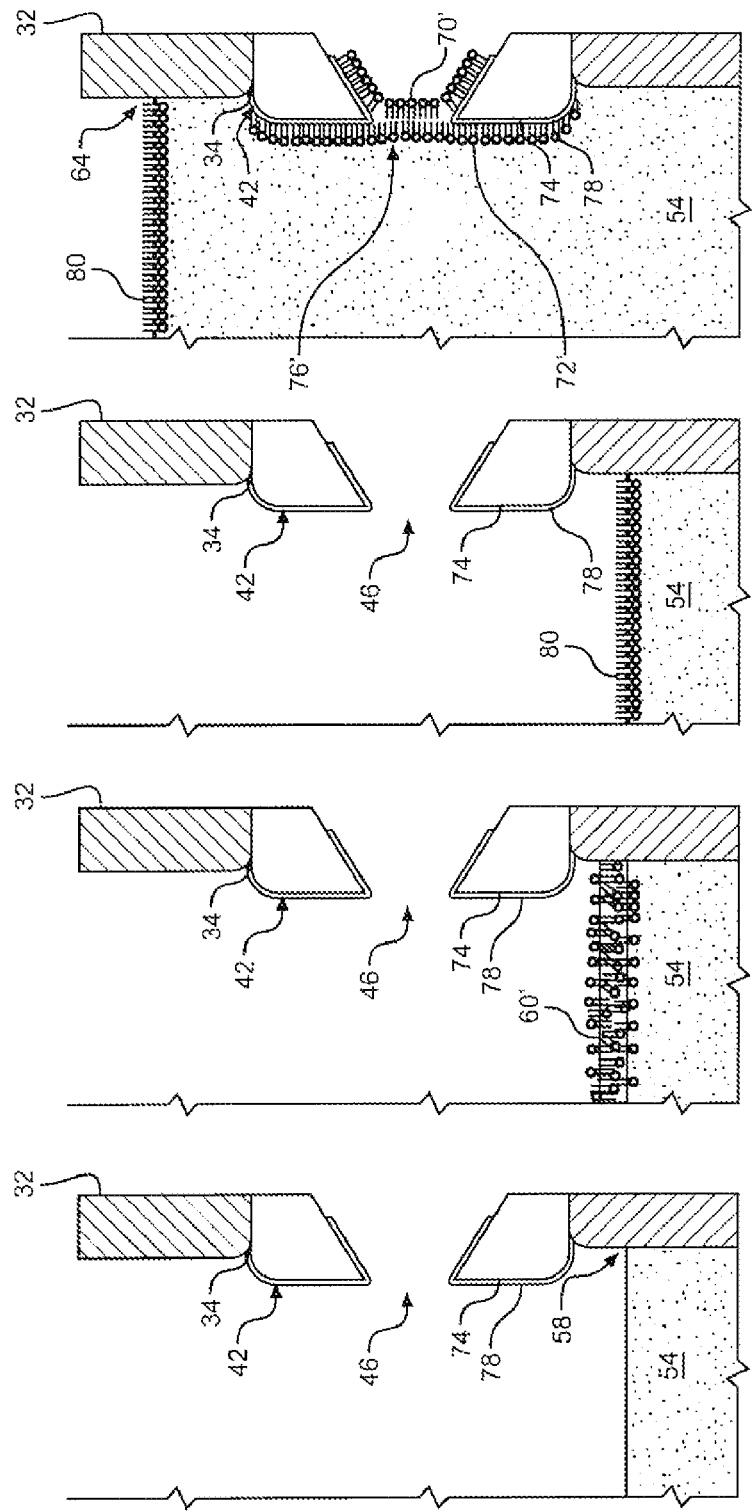

METHOD AND APPARATUS FOR SINGLE SIDE BILAYER FORMATION

CROSS-REFERENCE TO RELATED APPLICATIONS

The present application is represents a continuation of application Ser. No. 12/325,792, filed Dec. 1, 2008, now U.S. Pat. No. 8,124,191, which claims the benefit of U.S. Provisional Patent Application Ser. No. 60/991,542 entitled "Single Side Automated Bilayer Formation" filed Nov. 30, 2007.

STATEMENT REGARDING FEDERALLY SPONSORED RESEARCH OR DEVELOPMENT

This invention was made with government support under Contract FA9550-06-C-006 awarded by the U.S. Air Force Office of Scientific Research. The government has certain rights in the invention.

BACKGROUND OF THE INVENTION

1. Field of the Invention

The present invention pertains to the art of forming lipid bilayer membranes and, more particularly, to forming planar lipid bilayers across small orifices for use in ion channel sensing systems.

2. Discussion of the Prior Art

A planar lipid bilayer (PLB), also referred to as a black lipid membrane (BLM), is a membrane composed of lipids that spans an orifice in a synthetic support. PLBs are used extensively as a controlled environment for the study of ion channel function. Once a PLB is formed, ion channels can be inserted into the PLB by either the spontaneous insertion of water soluble ion channels from bulk solution or by the incorporation of ion channels by fusion of ion channel containing liposomes. Ion channels are membrane proteins that play a critical role in a vast number of physiological processes including neural signaling, muscle excitation, hormone secretion, blood pressure regulation, electrolyte balance and cell death. Due to their importance in such a broad range of physiological functions, the detailed function of ion channels, as well as their interaction with drugs and other chemicals, is a field of intensive scientific research. Ion channels are often studied in their natural cellular environment, but the PLB provides a far more controlled and accessible means to study the behavior of a wide range of ion channels.

Ion channels present in lipid bilayers are also useful as components of biosensors. The presence of specific chemicals and changes in environmental conditions, such as pH, electrolyte concentration, and temperature, affect the function of the ion channel. By monitoring the conductance of an ion channel, it is possible to detect the presence of a wide variety of chemical agents.

Nanometer and micron scale apertures, referred to as "nanopores", provide a robust platform for the formation of lipid bilayers and measurement of ion channel currents. The small area of bilayers formed on nanopores leads to long bilayer lifetimes, insensitivity to vibrations and a very low capacitance across the bilayer. The vibration insensitivity reduces the noise level of the ion channel measurement by eliminating coherent noise sources from the environment surrounding the apparatus. The low area of the bilayer minimizes current noise due to the conductance of time varying currents across the bilayer itself. Nanopores produced in glass and quartz substrates have an added advantage that the high resistance and low dielectric of the material further reduce the current noise of the ion channel measurement.

The lipids in a PLB are typically phospholipids, but bilayers may also be formed from a wide variety of lipids including glycerolipids, glycerophospholipids, sphingolipids, saccharolipids, prenol lipids, fats, fat acyls, sterols and polyketides. Typically, PLBs are formed across a single aperture (e.g., 10-200 µm in diameter) in a hydrophobic film (e.g., Delrin™, polystyrene, polysulfone, polymethyl methacrylate), or over a drawn glass patch pipette (e.g., 100 nm to 5 µm in diameter). A PLB can also be formed over a glass nanopore membrane (GNM), which is comprised of a single conical-shaped pore (10 nm to 2 µm radius orifice) embedded in a thin glass membrane (~50 µm), at the end of a cyano-silane coated glass capillary. PLBs have also been formed across apertures in silicon, silicon nitride and silicon oxide deposited on a semiconductor surface. The surface properties of the substrate utilized have a dramatic impact on the structure of the bilayer.

Currently, there are a number of methods of PLB formation known to those familiar with the art. These include: apposition, painting, tip dipping and microfluidics, which will be discussed in more detail below. In the apposition method, a hydrophobic film containing a single aperture is mounted between two compartments of a cell. The two compartments are then filled with an electrolyte solution so that the heights of the solutions are below the aperture. Next, the hydrophobic film is pretreated by placing a drop of hexadecane on the surface of the film in the vicinity of the aperture. A mixture of lipid/pentane is placed drop-wise on the surface of both electrolyte solutions and the pentane is given time to evaporate, leaving lipid monolayers on the surface of the electrolyte solutions. One electrolyte solution is then raised up past the aperture, depositing a lipid monolayer on the surface of the hydrophobic film and one leaflet of the bilayer that will span the aperture. The other electrolyte solution is then raised up past the aperture, depositing a lipid monolayer on the opposite side of the hydrophobic film, and the second leaflet of the bilayer which spans the aperture. This technique is well known to form solvent free bilayers, i.e., the PLB does not contain a significant amount of organic solvent. However, apposition cannot be utilized in systems wherein only one side of an aperture is accessible, e.g., a glass nanopore membrane or an array of nanopores with individual readouts.

The tip dip method is commonly used to place planar lipid bilayers over patch pipettes and involves first placing a patch pipette tip into a cell containing an electrolyte solution. A lipid/organic solvent mixture is then placed drop-wise on top of the electrolyte solution and is allowed to spread out, forming a lipid monolayer across the surface. Next, the patch pipette tip is pulled out of the electrolyte solution, which deposits a lipid monolayer on the surface of the pipette tip, with the hydrophilic head groups oriented towards the water layer on the glass surface. The pipette tip is then pushed back through the lipid monolayer at the air/water interface to deposit the second lipid monolayer onto the already existing monolayer and form a lipid bilayer. These lipid bilayers are known to contain a small fraction of organic solvent. Since the surface of the patch pipette is hydrophilic, the PLB extends past the orifice and around the side of the patch pipette. This extended bilayer allows ion channels to occupy the supported lipid bilayer on the glass in a region not over the aperture itself. Ion channels in this region will have a tendency to produce anomalously low conductances due to the high impedance of the water layer between the supported lipid bilayer and the glass.

The painting method involves the spreading of lipid/organic solvent across the surface of a hydrophobic film, using a pipette tip, in order to deposit a lipid bilayer across an aperture in that film. In the painting method, the surface of the film is initially "primed" with lipid/organic solvent. Typically, priming constitutes utilizing a pipette tip to deposit lipid/organic solvent onto the hydrophobic film. This lipid/ solvent is then lightly spread out across the surface of the film around the aperture and allowed to dry. After drying, the film is placed in a two compartment cell that is separated by the single aperture. Both sides of the cell are then filled with electrolyte solution so that the height of each solution lies above the aperture. The film is then primed a second time under solution. A clean pipette tip is then used to drag the lipid/solvent on the surface of the film across the aperture, spontaneously forming a lipid bilayer. The painting method is a manual process that requires considerable skill to accomplish and does not lend itself to automation. Additionally, the PLB formed by painting contains a large amount of solvent due to the nature of the process. High solvent levels in the PLB are known to affect the function of incorporated ion channels.

PLBs have also been formed in microfluidics devices. With this method, for instance, a 100 μm diameter aperture is created between an upper chamber and a 0.5 mm high by 2 mm wide channel. An aqueous electrolyte is added to the upper chamber and a lipid/solvent solution is flowed through the channel past the aperture. Air is passed through the channel to remove the lipid/solvent solution and an aqueous electrolyte is introduced to the channel. The outer chamber is sealed, a pressure is applied, and the PLB spontaneously forms across the aperture. The microfluidic PLB formation method requires a large number of steps and has not been shown to work for apertures under 100 μm in diameter.

The above-discussed bilayer formation methods either require significant training (e.g., painting and tip dip), large pore sizes, many steps or require open access to both sides of the aperture across which the bilayer is formed. Currently, there is no available method to reliably and automatically form lipid bilayers across an aperture when only one side of the aperture is accessible. Accordingly, there is seen to be a need in the art for a method and system in which lipid bilayers can easily and reproducibly be directly deposited even if access is restricted to only one side of the aperture.

SUMMARY OF THE INVENTION

The present invention is directed to an apparatus and method for single side planar lipid bilayer (PLB) formation across nanopores. The membrane forming apparatus of the present invention includes a first fluid chamber and a second fluid chamber extending through the sidewall of the first fluid chamber and separated therefrom by a barrier wall including a nanopore formed therein. In a preferred embodiment, the second fluid chamber is a glass capillary defining a glass nanopore membrane (GNM). Optionally, the apparatus can include a lid for selectively sealing the first fluid chamber and an automated fluid level regulator for selectively altering the fluid levels within the first fluid chamber.

The apparatus of the present invention can be utilized to create either solvent containing PLBs or solvent-free PLBs. In use, an electrolyte solution is inserted into the first and second fluid chambers. A lipid/organic solvent mixture is then placed drop-wise on the top of the electrolyte solution in the first fluid chamber and allowed to spread out over the surface of electrolyte solution to form a lipid/organic solvent layer. In a preferred embodiment, a solvent containing PLB is created using a lipid/organic solvent mixture constituted by 1, 2-diphytanoyl-sn-glycero-3-phosphocholine (DPhPC) in a lower volatility organic solvent such as decane, hexadecane, squalene and other alkanes. The level of electrolyte solution in the first fluid chamber is then adjusted with respect to the barrier wall such that the electrolyte solution and lipid/organic solvent layer are carried up past the barrier wall, thereby forming a solvent containing PLB across the nanopore on the surface of the barrier wall. When a solvent-free PLB is desired, the lipid/organic solvent mixture is constituted by a lipid in a high vapor pressure organic solvent, such as pentane. The high vapor pressure organic solvent is allowed to evaporate in order to form a lipid monolayer on the surface of the electrolyte solution prior to adjusting the level of electrolyte in the first fluid chamber. The level of the electrolyte solution is then adjusted such that the electrolyte solution and lipid monolayer are carried up past the barrier wall, thereby forming a solvent-free PLB across the nanopore on the surface of the barrier wall. A hydrophobic coating may be applied to the surface of the barrier wall prior to PLB formation in order to provide additional support to the PLB.

The apparatus of the present invention can also be utilized to create either solvent containing PLBs or solvent-free PLBs using lipid vesicles. In use, an electrolyte solution is inserted into the first and second fluid chambers. Lipid vesicles can either be already in the electrolyte solution added to the first chamber or lipid vesicles can be added to the electrolyte solution after the electrolyte solution is added to the first chamber. The lipid vesicles will then spontaneously form a lipid monolayer on the surface of the electrolyte. A low or a combined high and low vapor pressure organic solvent is then added to the top of the electrolyte solution to form a lipid/ organic solvent layer on the surface of the electrolyte. The level of electrolyte solution in the first fluid chamber is then adjusted with respect to the barrier wall such that the electrolyte solution and lipid/organic solvent layer are carried up past the barrier wall, thereby forming a solvent containing PLB across the nanopore on the surface of the barrier wall. When a solvent-free PLB formed using lipid vesicles is desired, lipid vesicles can either be already in the electrolyte solution added to the first chamber or lipid vesicles can be added to the electrolyte solution after the solution is added to the first chamber. The lipid vesicles will then spontaneously form a lipid monolayer on the surface of the electrolyte prior to adjusting the level of the electrolyte in the first fluid chamber. A low vapor pressure solvent may be put on the surface of the barrier wall prior to adjusting the level of the electrolyte solution. The level of the electrolyte solution is then adjusted such that the electrolyte solution and lipid monolayer are carried up past the barrier wall, thereby forming a solvent-free PLB across the nanopore on the surface of the barrier wall.

Electrolyte solution levels may be adjusted manually or utilizing the automated fluid level regulator. The automated fluid level regulator may be in the form of a pump and controller which selectively varies the level of electrolyte solution in the first fluid chamber to affect deposition of a PLB across the nanopore, or may be in the form of a tilting apparatus that tilts the first fluid chamber to affect deposition of a PLB across the nanopore.

The membrane forming apparatus of the present invention is particularly adapted for use in an ion channel sensing system. More specifically, ion channels or protein pores may be inserted into PLBs and the system utilized to analyze ion channel sensitivity. In use, a controller applies a voltage bias across first and second electrodes located in the respective first and second fluid chambers and current between the electrodes is measured. Optionally, the membrane forming apparatus can be used to form multiple PLBs across an array of nanopores. With this configuration, the sensing system is capable of separately recording the conductance of ion channels inserted into multiple PLBs.

Advantageously, the present apparatus and method avoids the significant learning curve associated with employing tip-dip and membrane painting techniques and provides a reliable means for forming lipid bilayers across an aperture when only one side of the aperture is accessible.

BRIEF DESCRIPTION OF THE DRAWINGS

FIGS. 1A-1C depict various stages of membrane formation in a membrane forming apparatus of the present invention;

FIGS. 2A-2B depict various fluid level stages in the membrane forming apparatus of FIGS. 1A-1C utilizing a tilting method of fluid level control;

FIGS. 4A-4D depict a partial cross-sectional view of a glass nanopore membrane during various stages of solvent-free planar lipid bilayer formation of the present invention;

DETAILED DESCRIPTION OF THE PREFERRED EMBODIMENTS

Figure 3A:
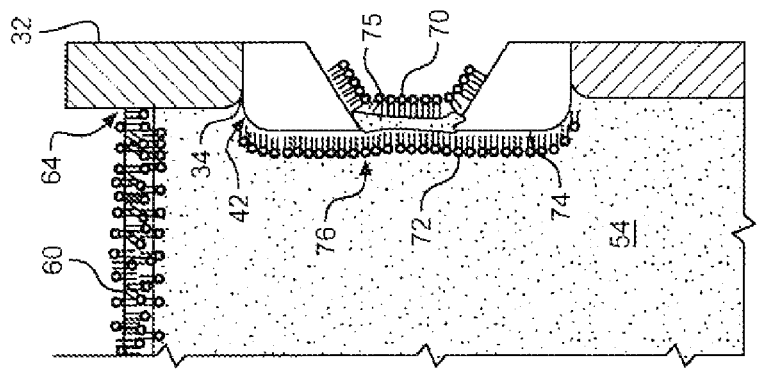
FIGS. 3A-3C depict a partial cross-sectional view of a glass nanopore membrane during various stages of solvent-containing planar lipid bilayer formation of the present invention.

In general, the present invention is directed to a system and method for formation of planar lipid bilayers (PLBs) across nanometer and micron scale apertures, i.e. nanopores. With initial reference to FIGS. 1A-1C, a membrane forming apparatus of the present invention for use in single-side bilayer formation is generally indicated at 20. Membrane forming apparatus 20 includes a first fluid cell or chamber 24 adapted to retain fluid, and a second fluid chamber 28 adapted to retain fluid. First fluid chamber 24 includes a bottom wall 30 and at least one sidewall 32 including at least one aperture 34 therein through which second fluid chamber 28 is connected. In a preferred embodiment, first fluid chamber 24 is a 1.25 cm×3 cm×2 cm Teflon® cell having a total capacity of approximately 7.5 cm$^3$. Second fluid chamber 28 also includes at least one sidewall 40 and a barrier wall 42 separating first fluid chamber 24 from second fluid chamber 28. In the preferred embodiment shown, second fluid chamber 28 is defined by a 1.6 mm O.D. soda-lime glass capillary having an inner diameter of 0.75 mm mounted in a polycarbonate pipette holder 44 fabricated by DAGAN Corp. Barrier wall 42 is provided with a nanopore 46 as depicted in FIGS. 3 and 4. Preferably, nanopore 46 is located approximately 0.5 cm from bottom wall 30 of first fluid chamber 24. Optionally, apparatus 20 can also include an automated fluid level regulator indicated at 50 for selectively altering the fluid level within first fluid chamber 24. When a glass capillary is utilized as shown, barrier wall 42 and nanopore 46 define a glass nanopore membrane (GNM). It should be appreciated that when a GNM system is utilized, access to one side of nanopore 46 is restricted. By restricted, it is meant that access to a side of nanopore 46 through second fluid chamber 28 is essentially inaccessible for purposes of membrane formation across nanopore 46.

In use, a first electrolyte solution 54 is inserted into first fluid chamber 24 to a first fluid level indicated at 58 and second fluid chamber 28 is filled with a second electrolyte solution 55. In a preferred embodiment, both electrolyte solution 54 and electrolyte solution 55 constitute a solution of 1M KCl in water buffered with 10 mM Tris buffer and hydrochloric acid (HCL) to bring the solution to a pH of 7.4. A lipid/organic solvent mixture is then placed drop-wise on the top of electrolyte solution 54 and allowed to spread out over the surface of electrolyte solution 54 to form a lipid/organic solvent layer 60 as depicted in FIG. 1B. The level of electrolyte solution 54 in first fluid chamber 24 is then adjusted with respect to barrier wall 42. In the embodiment shown in FIGS. 1A-1C, additional electrolyte solution 54 is added to first fluid chamber 24 to raise the fluid level of electrolyte solution 54 and lipid/solvent layer 60 from first fluid level 58 to a second fluid level 64, as depicted in FIG. 1C. The addition of electrolyte solution 54 into first fluid chamber 24 may be implemented manually, such as with a syringe, or mechanically utilizing fluid level regulator 50. In one embodiment, fluid level regulator 50 includes a conduit in fluid communication with first fluid chamber 24 and connected to a fluid source via a pump and controller for automatically adding and/or subtracting a desired amount of electrolyte solution 54 to/from the system. The controller can be programmed to maintain one of two solution levels within first fluid chamber 24, with one level being above nanopore 46 and one level below nanopore 46.

In an alternative embodiment depicted in FIGS. 2A and 2B, a fluid level regulator 50' preferably includes a mechanical device for tilting fluid chamber 24. In this embodiment, the level of electrolyte solution 54 is altered relative to barrier 42 and nanopore 46 by tilting first fluid chamber 24 at an angle relative to the vertical before the addition of lipid/organic solvent layer 60, then tilting first fluid chamber 24 to a horizontal position such that the level of electrolyte solution 24 and lipid/organic solvent layer 60 is raised from a first fluid level 58' below barrier wall 42 to a second fluid level 64' above barrier wall 42 as first fluid chamber 24 is re-positioned. Optionally, apparatus 20 can include a lid 66 for selectively sealing first fluid chamber 24 and preventing spills.

With this arrangement, PLB's are formed over barrier wall 42 by altering the level of electrolyte solution 54 and lipid/organic solvent layer 60 as will be discussed in more details below. Although the membrane forming method of the present invention will be discussed with reference to a GNM system, it should be understood that apparatus 20 can be utilized with any nano or micron scale orifice in a hydrophobic film or synthetic support structure (e.g., barrier wall 42) that possesses appropriate hydrophobicity or hydrophilicity for maintaining a lipid monolayer or bilayer, such as silicon, glass, quartz, silicon nitride, and orifices in hydrophobic plastics (e.g., Teflon®, polyethylene, Delrin™, polystyrene, polysulfone, etc). Regardless of the substrate, any nanopores 46 formed in barrier wall 42 will preferably have a diameter between 10 nm and 500 μm and, most preferably, between 100 nm and 2 μm. The present method provides for either: 1) the formation of suspended PLBs in which monolayers of lipid are deposited on a hydrophobic supporting surface that zip together to form a bilayer which spans only the orifice; or 2) supported PLBs, in which a bilayer lies on top of a hydrophilic support structure and orifice. The formation of both bilayer structures depends solely on the surface properties of the support structure, and is not limited by the bilayer formation method of the present invention.

Figure 3B:
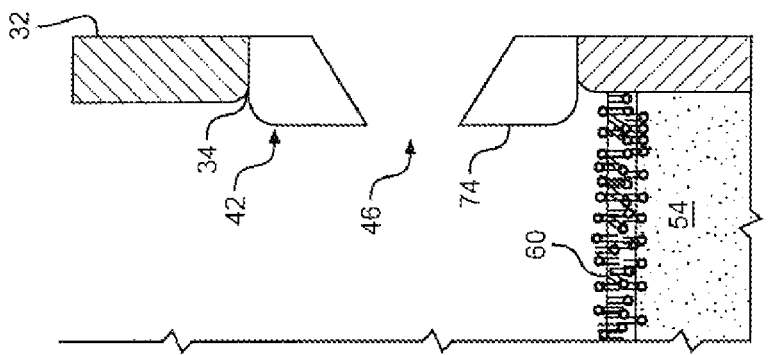
Figure 3C:
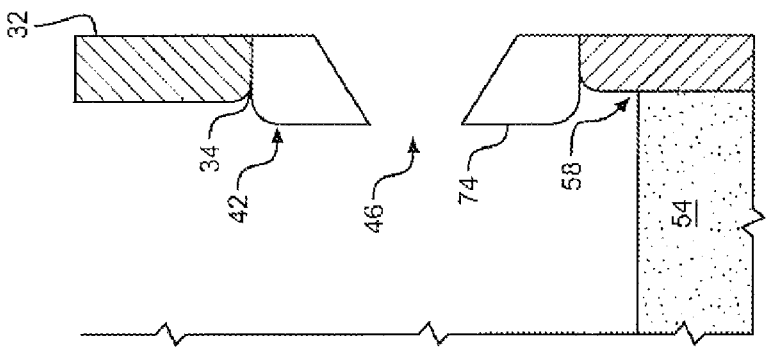

The formation of a solvent containing planar lipid bilayer 76 will now be discussed with reference to FIGS. 3A-3C. Again, electrolyte solution 54 is introduced into first fluid chamber 24 to establish a first fluid level 58 as depicted in FIG. 3A. A lipid/organic solvent solution, e.g., approximately 0.1 to 1 μL, is then introduced to the surface of electrolyte solution 54 and allowed to spread out over the surface of electrolyte solution 54 to form lipid/organic solvent layer 60. Preferably, lipid/organic solvent layer 60 constitutes 2-diphytanoyl-sn-glycero-3-phosphocholine (DPhPC) lipid in a low volatility organic solvent such as decane, hexane, hexadecane, squalene, other alkanes, and mixtures thereof. Most preferably, lipid/organic solvent layer 60 constitutes DPhPC lipid in 100% decane or DPhPC lipid in a mixture of 99% decane and 1% hexadecane. Additional electrolyte solution is then added to first fluid chamber 24 to raise the level of electrolyte solution 54 and lipid/organic solvent layer 60 from first fluid level 58 below nanopore 46 to second fluid level 64 above nanopore 46. As lipid/organic solvent layer 60 moves past barrier wall 42, a small amount of lipid (indicated at 70) crosses through nanopore 46 in barrier wall 42, and additional lipids spontaneously assemble into a monolayer 72 on an outer surface 74 of barrier wall 42, leaving a small amount of solvent 75 between lipid layers 70 and 72 to form an organic solvent containing PLB 76 suspended across nanopore 46. Preferably, outer surface 74 extends in a plane which ranges from approximately vertical up to 60° from vertical. In an alternative method, electrolyte 54 is raised above barrier wall 42 before forming lipid/organic solvent layer 60, lipid/organic solvent layer 60 is lowered below barrier wall 42, and the electrolyte level is again raised to carry lipid/organic solvent layer 60 across barrier wall 42 to spontaneously form PLB 76. Apparatus 20 allows one or more PLBs 76 to be consistently reproduced by simply lowering electrolyte solution 54 below outer surface 74 of barrier wall 42 and then raising electrolyte solution 54 above outer surface 74 of barrier wall 42.

As discussed above, the PLB formation may also be accomplished by tilting first fluid chamber 24 so that electrolyte solution 54 and lipid/organic solvent layer 60 are moved from a first fluid level 58' below nanopore 46 to a second fluid level 64' above nanopore 46. PLB 76 may be repeatedly broken and reformed by tilting first fluid chamber 24 to bring the level of lipid/organic solvent layer 60 below the level of barrier wall 42 and tilting first fluid chamber 24 back to a position where the level of lipid/organic solvent layer 60 is above barrier wall 42. Regardless of the method of fluid level adjustment utilized, barrier wall 42 may be provided with a coating 78 before fluid level adjustment, as depicted in FIGS. 4A-4C, to aid in membrane formation and retention. Coating 78 may be in the form of a hydrophobic coating and/or low vapor pressure organic solvent, such as squalene or hexadecane.

At this point, it should be mentioned that the formation of solvent containing lipid bilayer 76 could also be accomplished utilizing lipid vesicles. With this arrangement, electrolyte solution 54 is again introduced into first fluid chamber 24 to establish a first fluid level 58. Lipid vesicles (not shown) are then added to the electrolyte solution 54 and allowed to spontaneously form a lipid monolayer on the surface of electrolyte solution 54. Alternatively, the lipid vesicles can already be contained in the electrolyte solution 54 before the solution is added to the first fluid chamber 24. Preferably, the lipid vesicles constitute 2-diphytanoyl-sn-glycero-3-phosphocholine (DPhPC) lipid vesicles. A low volatility solvent is then added to the surface of the electrolyte solution to form a lipid/organic solvent layer corresponding to layer 60. More preferably, a low volatility solvent and high volatility solvent are then added to the surface of the electrolyte solution to form the lipid/organic solvent layer. Additional electrolyte solution is then added to first fluid chamber 24 to raise the level of electrolyte solution 54 and the lipid/organic solvent layer from first fluid level 58 below nanopore 46 to second fluid level 64 above nanopore 46. As the lipid/organic solvent layer moves past barrier wall 42, a small amount of lipid, such as indicated at 70, crosses through nanopore 46 in barrier wall 42, and additional lipids spontaneously assemble into a monolayer 72 on an outer surface 74 of barrier wall 42, leaving a small amount of solvent 75 between lipid layers 70 and 72 to form an organic solvent containing PLB 76 suspended across nanopore 46. Preferably, outer surface 74 extends in a plane which ranges from approximately vertical up to 60° from vertical. In an alternative method, electrolyte 54 is raised above barrier wall 42 before forming the lipid/organic solvent layer, the lipid/organic solvent layer is lowered below barrier wall 42, and the electrolyte level is again raised to carry the lipid/organic solvent layer across barrier wall 42 to spontaneously form PLB 76. Apparatus 20 allows one or more PLBs 76 to be consistently reproduced by simply lowering electrolyte solution 54 below outer surface 74 of barrier wall 42 and then raising electrolyte solution 54 above outer surface 74 of barrier wall 42.

The formation of a solvent-free PLB 76' will now be discussed with reference to FIGS. 4A-4D. Initially, electrolyte solution 54 is introduced into first fluid chamber 24 to establish a first fluid level 58. A solution of lipid in a high vapor pressure organic solvent is then introduced to the surface of electrolyte solution 54 and allowed to spread out over the surface of electrolyte solution 54 to form lipid/organic solvent layer 60' as depicted in FIG. 4B. Preferably, lipid/organic solvent layer 60' constitutes lipid in pentane. The lipid forms a monolayer at the interface between the organic solvent and electrolyte 54. Solvent layer 60' is then allowed to sit for a period of time sufficient to allow for evaporation of the high vapor pressure organic solvent (e.g., pentane), thereby leaving a lipid monolayer 80 as depicted in FIG. 4C. Electrolyte solution 54 is then added to first fluid chamber 24 to raise the level of electrolyte solution 54 and lipid monolayer 80 from first fluid level 58 below nanopore 46 to second fluid level 64 above nanopore 46. In the embodiment shown, coating 78 is applied to barrier wall 42 prior to altering the fluid level within first fluid chamber 24. As lipid monolayer 80 moves past barrier wall 42, a small amount of lipid, indicated at 70' crosses through nanopore 46 in barrier wall 42, and additional lipids spontaneously assemble into a monolayer 72' on coating 78 of barrier wall 42 to form a solvent-free PLB 76' suspended across nanopore 46. Alternatively, the PLB formation process may be accomplished utilizing the tilting method of fluid level control discussed above.

In a manner similar to that described above with respect to the potential to form planar lipid layer 70 using lipid vesicles, the solvent-free PLB can also be formed using lipid vesicles. In this situation, electrolyte solution 54 would be initially introduced into first fluid chamber 24 to establish a first fluid level 58. Lipid vesicles (not shown) are then added to the electrolyte solution 54 and allowed to spontaneously form a lipid monolayer on the surface of electrolyte solution 54. Alternatively, the lipid vesicles can already be contained in the electrolyte solution 54 before the solution is added to the first fluid chamber 24. Preferably, the lipid vesicle constitutes 2-diphytanoyl-sn-glycero-3-phosphocholine (DPhPC) lipid vesicles. Electrolyte solution 54 is then added to first fluid chamber 24 to raise the level of electrolyte solution 54 and the lipid monolayer from first fluid level 58 below nanopore 46 to second fluid level 64 above nanopore 46. As before, coating 78 is applied to barrier wall 42 prior to altering the fluid level within first fluid chamber 24. As the lipid monolayer moves past barrier wall 42, a small amount of lipid, such as indicated at 70', crosses through nanopore 46 in barrier wall 42, and additional lipids spontaneously assemble into a monolayer 72' on coating 78 of barrier wall 42 to form solvent-free PLB 76' suspended across nanopore 46. Alternatively, the PLB formation process may be accomplished utilizing the tilting method of fluid level control discussed above.

Figure 5:
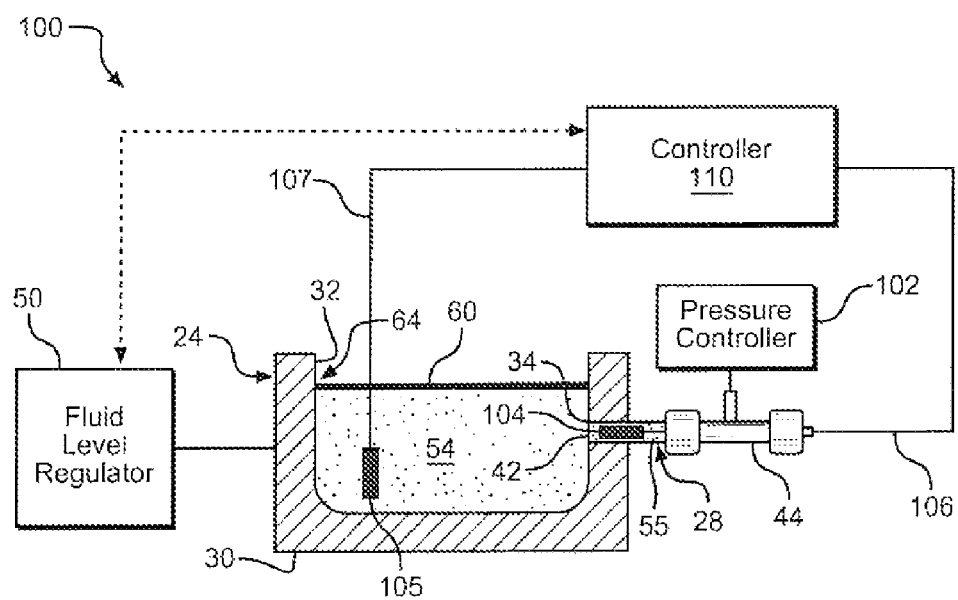
FIG. 5 is a schematic depiction of an ionic conductive measurement system of the present invention incorporating the membrane forming apparatus of FIGS. 1A-1C.

PLB's formed by single side bilayer formation are suitable for ion channel/protein pore reconstitution and/or liposome fusion. In a preferred embodiment of the present invention, apparatus 20 is utilized in an ion channel sensing system depicted at 100 in FIG. 5. More specifically, once PLB 76, 76' is in place, ion channels or protein pores (not shown) may be inserted into PLB 76, 76' in a manner known in the art, and system 100 may be utilized to analyze ion channel sensitivity. Typically, a positive pressure of 20 to 300 mm Hg is applied to second fluid channel 28 by a pressure controller 102 connected to holder 44 after PLB formation in order to induce insertions of ion channels into the PLB suspended over nanopore 46, while preferably either a negative or positive back pressure is applied to stop ion channel activity. A first electrode 104 is inserted into second fluid chamber 28 such that it is immersed in the electrolyte solution 55 and a second electrode 105 is submerged in the electrolyte solution 54 of first fluid chamber 24. First and second electrodes 104 and 105 are connected via electrical conductors 106 and 107 respectively to a controller 110 which is adapted to apply a constant or time varying voltage bias across first and second electrodes 104 and 105 and measure the electrical current between first and second electrodes 104 and 105. First and second electrodes 104 and 105 are preferably silver-silver chloride (Ag/AgCl) electrodes produced by exposing silver wires to a bleach solution, although other types of electrodes may be used including those composed of silver, silver chloride, platinum, carbon, gold and any other compounds known in the art.

In an alternate embodiment, fluid level regulator 52 can be connected to controller 110 via feedback control, as indicated by the dotted line interconnecting fluid level regulator 52 to controller 110. This will allow the solution height within the cell 24 to be automatically adjusted, based on the conductance being measured between the two electrodes 104, 105, across the nanopore 46 in the barrier wall 42.

In one feedback embodiment, the solution height 54 initially lies below the barrier wall 42 and nanopore 46. Lipid/organic solvent 60 is appropriately deposited. The conductance between the two electrodes is immeasurably low, as there is no electrical connection between the two electrodes 104, 105 (open circuit). In this case, the fluid level regulator 52 will begin to automatically raise the solution height of the electrolyte solution. As the solution height crosses over the barrier wall 42, across the nanopore 46, depositing a PLB, the conductance between the two electrodes 104, 105 will become measurable, between 0.1 pS and 2 fS, this value is dependent on the electrolyte solution strength, the size of the nanopore, the lipid used, and the organic solvent used. Once a measurable conductance is measured the controller will continue to raise the electrolyte solution height, for a set amount of volume, such that the electrolyte surface lies above the barrier wall and nanopore.

In the second feedback embodiment, the solution height 55 lies above the barrier wall 42 and the nanopore 46. Lipid/organic solvent is appropriately deposited 60. The conductance between the two electrodes 104 105 is measurable, between 20 pS and 0.1 mS, depending on the electrolyte solution strength and the size of the nanopore. Based on the measured conductance value, the fluid level regulator 52, via feedback, will begin to lower the electrolyte solution height. Once the electrolyte solution has dropped past the barrier wall and the nanopore, as measured by a drop in conductance (<2 fS) between the two electrodes, the solution will be raised back up past the barrier wall, depositing the PLB over the nanopore, as measured by a conductance value between 0.1 pS and 2 fS. The two feedback embodiments described above can also be used repeatedly together, in order to automatically reform bilayers across the nanopore, should they break.

Figure 6:
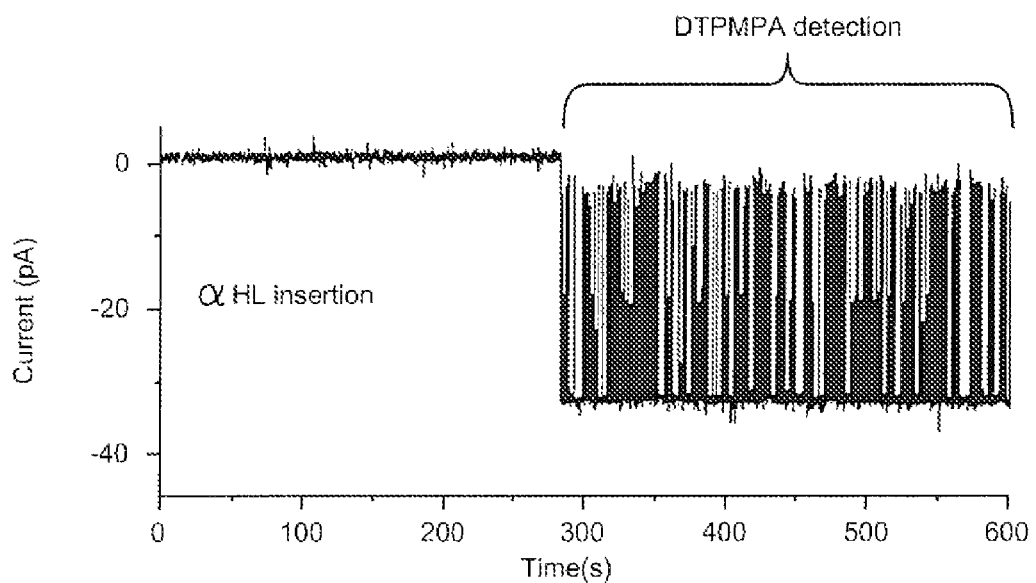
FIG. 6 is a graph depicting the detection of an organic molecule in solution utilizing a recombinant alpha hemolysin ion channel inserted into a PLB formed according to the method of the present invention.

FIG. 6 depicts the change in measured current due to the insertion of a recombinant αHL ion channel into a PLB formed by single side bilayer formation in accordance with the present invention. The recombinant αHL channel is different from the wild type αHL (WT-αHL) channel in that the methionine residue at the 113 position of each monomer has been replaced by lysine. After the spontaneous insertion of the recombinant ion channel, the ion channel retains its inherent activity as depicted by the detection of the organic molecule Diethylene Triamine Penta (Methylene Phosphonic Acid) heptasodium salt (DTPMPA).

Figure 7:
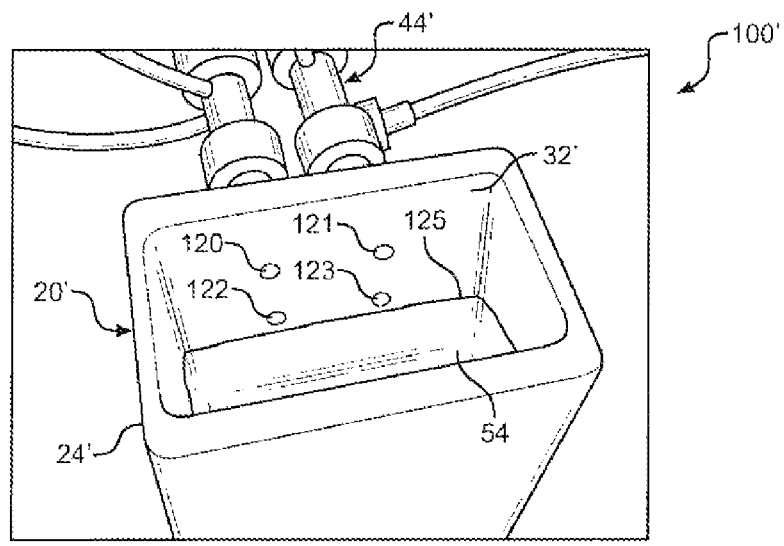
FIG. 7 depicts an ionic conductive measurement system of the present invention including an array of four glass nanopore membranes.

The PLB formation apparatus 20 can also be used to form multiple PLBs across an array of nanopores. For example, as depicted in FIG. 7, a membrane forming apparatus 20' for forming an array of membranes is utilized in an ion channel sensing system 100'. Apparatus 20' is shown including four GNMs 120-123 inserted through a sidewall 32' in a first fluid chamber 24'. Each GNM 120-123 is housed within a separate holder 44' that allows for a backpressure to be applied to the interior of each GNM 120-123. Each GNM 120-123 is filled with an electrolyte solution and separate electrodes (not shown) are inserted into each GNM 120-123 in such a manner that each electrode is immersed in the electrolyte solution within the respective GNM 120-123. Electrolyte solution 54 is added to first fluid chamber 24' to a first fluid level below all of the GNMs, as indicated at 125. A single electrode (not shown) is then inserted into electrolyte solution 54 of first fluid chamber 24'. The electrodes within GNMs 120-123 and the reference electrode in first fluid chamber 24' are connected to a controller, such as controller 110 depicted in FIG. 5, that is capable of applying a separate and distinct voltage bias between each of the electrodes within GNMs 120-123 and the reference electrode in first fluid chamber 24'. The controller is also capable of measuring the current between each of the electrodes within GNMs 120-123 and the reference electrode in first fluid chamber 24'. PLB's are then formed across the surface of GNMS 120-123 utilizing the membrane forming method described above. More specifically, a lipid/organic solvent mixture is deposited onto the surface of electrolyte solution 54 and the level of electrolyte solution is raised past the array of GNMs 120-123, spontaneously forming PBL's across each individual GNM 120-123. Ion channels are then inserted into the bilayer spanning the nanopore 46 of each GNM via vesicle fusion or spontaneous insertion from solution in a manner known in the art. With this configuration, sensing system 100' is capable of separately recording the conductance of ion channels inserted into the PLBs of multiple GNMs.

Figure 8:
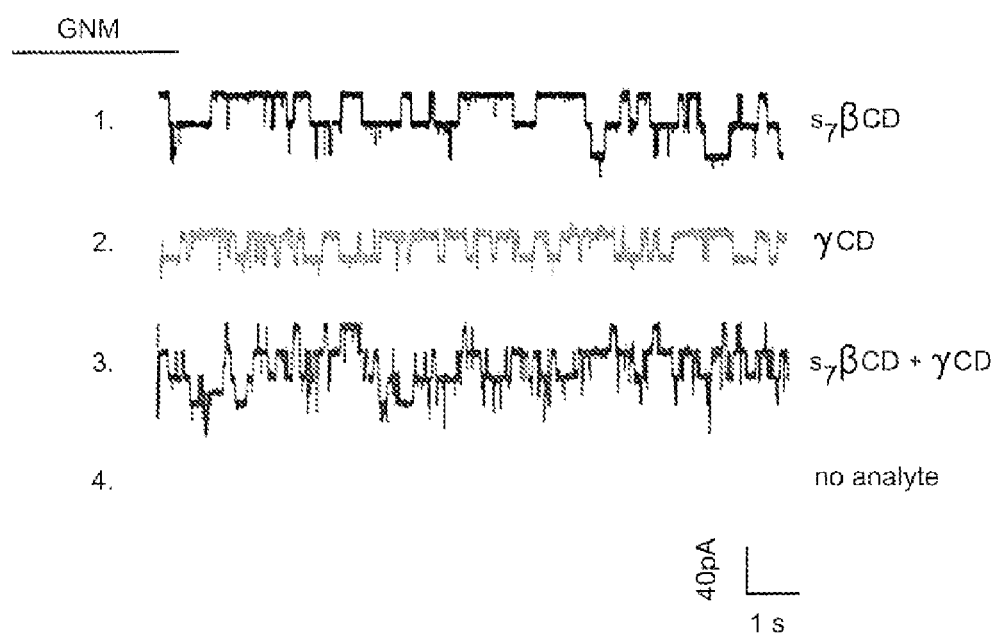
FIG. 8 depicts electrical readout results of the ionic conductive measurement system of FIG. 7.

An example of ion channel recordings utilizing sensing system 100' of the present invention are depicted in FIG. 8. In this example, first fluid chamber 24' was constructed of Teflon and had reservoir dimensions of 35 mm deep, 35 mm wide and 25 mm long. GNMs 120-123 were positioned on a wide face 32' of first fluid chamber 24', as indicated in FIG. 7. With the electrolyte solution 54 below the level of GNMs 120-123, a small amount (0.5 to 1 µl) of 5 mg/ml DPhPC lipid in decane was placed on the surface of electrolyte solution 54 comprised of 1 M KCl, 10 mM potassium phosphate buffer (PPB) (pH 7.2). The electrolyte solution surface was then raised up past each GNM 120-123, simultaneously depositing suspended lipid bilayers onto each GNM 120-123. Once all four GNMs 120-123 contained bilayers, WT-αHL monomer was added to the test cell to a final concentration of approximately 400 nM. Following the addition of WT-αHL, the back pressure of each GNM 120-123 was increased near its respective break pressure (determined prior to adding WT-αHL). Once WT-αHL was inserted into the PLB 76 across the nanopore 46 of a particular GNM 120-123, the back pressure of that GNM 120-123 was decreased to near the pull-out pressure. If the WT-αHL came out of the bilayer, the pressure was again raised to near its respective break pressure. This process was continued until all four bilayers spanning the nanopores in GNMs 120-123 contained one to a few αHL channels. Each GNM 120-123 was filled with the electrolyte solution (1 M KCl, 10 mM PPB, pH 7.2) or the electrolyte solution and one or more additional compounds of interest. Specifically, GNM 120 contained 50 µM beta-Cyclodextrin, sulfated Sodium salt ($s_7\gamma CD$) (CAS #37191-69-8); GNM 121 contained 50 µM gamma-Cyclodextrin ($\gamma CD$) (CAS #17465-86-0); GNM 122 contained, 50 µM $s_7\gamma CD$ and 50 µM $\gamma CD$; and GNM 123 contained only the electrolyte solution. A voltage bias of 40 mV was applied between the internal electrodes of each GNM 120-123 and the reference electrode in first fluid chamber 24'. The separate recordings of the electric current through ion channels in the PLBs of each of the four GNMs 120-123 are those shown in FIG. 8.

It should be understood that the apparatus and method of the present invention provides a reliable means for forming lipid bilayers across an aperture when only one side of the aperture is accessible. Advantageously, the present apparatus and method avoids the significant learning curve associated with utilizing tip-dip and membrane painting techniques. Although described with reference to preferred embodiments of the invention, it should be readily understood that various changes and/or modifications can be made to the invention without departing from the spirit thereof. Of particular note, it should be realized that the disclosed coating used to form the various layers can be used for bilayer formation with a solvent as well as solvent free. For instance, the coating could already exist on the nanopore membrane and then a low volatility solvent, such as hexadecane, could be then added. Therefore, it must be recognized that the coating disclosed really encompasses at least one coating which itself can be constituted by multiple levels or sub-coatings. In general, the invention is only intended to be limited by the scope of the following claims.

We claim:

1. A method for single-side formation of a planar lipid bilayer in a single-side membrane forming apparatus comprising a first fluid chamber having a bottom wall and a sidewall, and a second fluid chamber having a sidewall and a barrier wall separating the first fluid chamber from the second fluid chamber and including at least one nanopore formed therein, wherein at least a portion of the barrier wall has a surface property constituted by hydrophobicity or hydrophilicity, the method comprising:
    adding an electrolyte to the first fluid chamber to establish a level of electrolyte in the first fluid chamber;
    adding an electrolyte to the second fluid chamber;
    adding a lipid solution to the electrolyte in the first fluid chamber to form a lipid layer on a surface of the electrolyte; and
    adjusting the level of electrolyte within the first fluid chamber relative to the nanopore such that the lipid layer is carried across a surface of the barrier wall, causing spontaneous single-side formation from the first fluid chamber of a planar lipid bilayer across the nanopore, wherein a top level of the electrolyte in the second fluid chamber remains above the nanopore during the spontaneous single-side formation of the planar lipid bilayer.

2. The method of claim 1, wherein the surface property of the portion of the barrier wall is hydrophobicity.

3. The method of claim 2, wherein the surface property hydrophobicity is obtained by applying a hydrophobic coating to the portion of the barrier wall.

4. The method of claim 3, wherein the hydrophobic coating extends into the second fluid chamber.

5. The method of claim 3, wherein the hydrophobic coating is a cyano-silane.

6. The method of claim 2, wherein the planar lipid bilayer across the nanopore is comprised of monolayers of lipid on the portion of the barrier wall and a bilayer of lipid suspended across the nanopore.

7. The method of claim 1, wherein the surface property of the portion of the barrier wall is hydrophilicity.

8. The method of claim 7, wherein the planar lipid bilayer across the nanopore lies on top of both the barrier wall and the nanopore.

9. The method of claim 1, wherein adjusting the level of electrolyte constitutes increasing the amount of electrolyte within the first fluid chamber such that the lipid layer is carried across the surface of the barrier wall as the level of electrolyte within the first fluid chamber is raised from a level below the nanopore to a level above the nanopore.

10. The method of claim 1, wherein adjusting the level of electrolyte constitutes decreasing the amount of electrolyte within the first fluid chamber such that the lipid layer is lowered from a level above the nanopore to a level below the nanopore, then increasing the amount of electrolyte within the first fluid, chamber such that the lipid layer is raised from the level below the nanopore to a level above the nanopore such that the lipid layer is carried across the surface of the barrier wall as the level of electrolyte within the first fluid chamber is raised above the nanopore.

11. The method of claim 1, wherein adjusting the level of electrolyte constitutes tilting the first fluid chamber such that the level of electrolyte changes relative to the nanopore, and carries the lipid layer over the surface of the barrier wall.

12. The method of claim 1, wherein the lipid solution contains at least one low volatility organic solvent.

13. The method of claim 1, wherein the lipid solution contains a mixture of lipids.

14. The method of claim 1, wherein the lipid solution contains at least one high volatility organic solvent.

15. The method of claim 14, further comprising waiting a period of time, after the lipid solution has been added, to allow the high volatility organic solvent to evaporate and a lipid monolayer to form prior to adjusting the level of electrolyte within the first chamber.

16. The method of claim 1, wherein the lipid solution contains lipid vesicles.

17. The method of claim 1, further comprising coating the barrier wall with a hydrophobic coating about a periphery of the nanopore prior to adjusting the level of electrolyte within the first fluid chamber.

18. The method of claim 17, wherein the hydrophobic coating is a low volatility organic solvent.

19. The method of claim 1, further comprising: restricting access to a side of the nanopore through the second fluid chamber.

* * * * *